United States Patent [19]

Wilson et al.

[11] Patent Number: 4,493,771

[45] Date of Patent: Jan. 15, 1985

[54] SCALE INHIBITING WITH COMPOUNDS CONTAINING QUATERNARY AMMONIUM AND METHYLENEPHOSPHONIC ACID GROUPS

[75] Inventors: David A. Wilson, Richwood; Wilfred W. Wilson, Lake Jackson, both of Tex.

[73] Assignee: The Dow Chemical Company, Midland, Mich.

[21] Appl. No.: 586,596

[22] Filed: Mar. 6, 1984

Related U.S. Application Data

[62] Division of Ser. No. 489,442, Apr. 28, 1983, Pat. No. 4,459,241.

[51] Int. Cl.$^3$ ............................................. C02F 5/14
[52] U.S. Cl. .................................... 210/700; 252/180
[58] Field of Search ............... 210/698, 699, 700, 701; 252/82, 86, 87, 180, 181; 260/502.5 E

[56] References Cited

U.S. PATENT DOCUMENTS

| | | | |
|---|---|---|---|
| 2,847,442 | 8/1958 | Sallmann | 260/502.5 E |
| 3,336,221 | 8/1967 | Ralston | 210/700 |
| 3,434,969 | 3/1969 | Ralston | 210/700 |
| 3,859,211 | 1/1975 | Redmore | 210/729 |
| 3,867,286 | 2/1975 | Quinlan | 210/700 |
| 4,075,243 | 2/1978 | Quinlan | 260/502.5 E |
| 4,234,511 | 11/1980 | Buckman | 260/502.5 E |
| 4,330,487 | 5/1982 | Redmore | 210/700 |

Primary Examiner—Ernest G. Therkorn
Attorney, Agent, or Firm—A. C. Ancona

[57] ABSTRACT

Compounds having improved properties of inhibiting the precipitation of metal ions when used in threshold amounts have been made which are derivatives of ammonia or di- or polyamines in which the amine hydrogens have been substituted with both methylenephosphonic acid groups or their salts and hydroxypropyl quaternaryammonium halide groups. Thus, ammonia can have two hydrogens replaced with methylenephosphonic groups while the third is replaced with a hydroxypropyltrimethylammonium chloride group; and three hydrogens of ethylenediamine can be replaced with methylenephosphonic groups, the fourth being replaced with a hydroxypropyltrimethylammonium chloride group.

7 Claims, No Drawings

SCALE INHIBITING WITH COMPOUNDS CONTAINING QUATERNARY AMMONIUM AND METHYLENEPHOSPHONIC ACID GROUPS

CROSS-REFERENCE TO RELATED APPLICATION

This is a divisional of application Ser. No. 489,442, filed Apr. 28, 1983, now U.S. Pat. No. 4,459,241.

BACKGROUND OF THE INVENTION

The use of methylenephosphonic acid substituted alkylene polyamines for metal ion control at less than stoichiometric amounts was suggested in a patent to Bersworth (U.S. Pat. No. 2,609,390) in 1952. Later a water dispersible polymeric amine chelating agent which included alkylene phosphonate derivatives was indicated as having "threshold" effects in scale inhibition applications (see U.S. Pat. No. 3,331,773), this term being used to describe the use of the agent in less than stoichiometric amounts. The diamine and polyamine methylenephosphonate derivatives are taught and claimed in U.S. Pat. Nos. 3,336,221 and 3,434,969, respectively. Some of the products disclosed in these two patents are available commercially and are recommended as scale inhibitors when applied in threshold amounts.

Some other patents disclose heterocyclic nitrogen containing compounds which are useful as chelating agents and may be employed in threshold amounts are U.S. Pat. Nos. 3,674,804; 3,720,498; 3,743,603; 3,859,211; and 3,954,761.

Methylenephosphonates of polyalkylene polyamines, disclosed in U.S. Pat. No. 4,051,110, are made by reacting di- or polyamines with a chain extending agent such as a dihalide or an epoxyhalide, e.g. ethylene dichloride or epichlorohydrin and thereafter, with phosphorous acid and formaldehyde. Thus, for example, triethylenetetramine is reacted with epichlorohydrin in an approximately one to one mole ratio; thereafter the product is reacted with phosphorous acid, and formaldehyde in the presence of hydrochloric acid. The resulting methylenephosphonated polyamine is useful in small amounts as a scale inhibitor, being employed at concentrations of 20–50 ppm.

Certain phosphonic acid derivatives of the aliphatic acids can be prepared by reacting phosphorous acid with acid anhydrides or acid chlorides, e.g. the anhydrides or chlorides of acetic, propionic and valeric acids. The compounds prepared have the formula

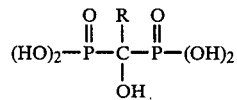

wherein R is a lower alkyl radical having 1 to 5 carbon atoms. The method of making and using these products is described in U.S. Pat. No. 3,214,454. The use of threshold amounts to prevent calcium precipitation is disclosed and claimed therein.

Compounds such as the reaction product of a halohydrin, e.g. epichlorohydrin, with an amine, e.g. trimethylamine, give quaternary ammonium chlorohydrin adducts, which have biological activity. The chlorine of the chlorohydrin moiety can, of course, be reacted with another amine to give a hydroxyalkyl quaternary ammonium compound and adduct of the amine.

It has now been discovered that such a functionality when attached to a diamine or polyamine which also contains a methylenephosphonic acid group will give a compound having improved threshold activity, i.e. inhibits precipitation of metal ions from solution at less than stoichiometric amounts.

SUMMARY OF THE INVENTION

Compounds having improved properties of inhibiting the precipitation of metal ions when used in threshold amounts have been made which are derivatives of ammonia or di- or polyamines in which the amine hydrogens have been substituted with both methylenephosphonic acid groups or their salts and hydroxypropyl quaternaryammonium halide groups. These compounds have the formula

wherein A, B, C and D substituents are independently selected from hydrogen, methylenephosphonic acid, or salts thereof, hydroxypropyltrialkylammonium halide, wherein the trialkylammonium moiety contains alkyl groups having from 1 to 5 carbon atoms and n is 0 to 15, and wherein said substituents include at least one methylenephosphonic acid group, or salt thereof, and at least one 2-hydroxy-3 (trialkylammonium halide) propyl group.

DETAILED DESCRIPTION OF THE INVENTION

The compounds of the present invention are substituted amines in which at least one of the amine hydrogens is substituted with a methylenephosphonic acid group or salts thereof and at least one with a quaternary ammonium radical.

The following examples are representative of making the compounds of the invention and of making the completely phosphonated compounds for comparison.

EXAMPLE 1

Ethylenediamine (EDA) (15 g, 0.25 mole) and 94 g (0.25 mole) of a 50% aqueous solution of 3-chloro-2-hydroxypropyltrimethylammonium chloride were added to a 500 ml round-bottom reaction flask equipped with a water-cooled reflux condenser, mechanical stirrer, thermometer with a temperature controller, and an addition funnel. The reaction mixture was heated to 90° C. and digested for about one hour and cooled. Approximately 60 g of concentrated hydrochloric acid solution and 67.5 g (0.82 mole) of phosphorous acid were added to the reaction flask and heated to reflux and maintained for one hour. Aqueous 37% formaldehyde solution (67.4 g, 0.83 mole) was weighed into the addition funnel and added over a two-hour period. The reaction mixture was heated at reflux for an additional three hours and then cooled. The product was the derivative of EDA in which one hydrogen had been replaced with 2-hydroxypropyltrimethylammonium chloride groups and the remaining hydrogens with methylenephosphonic acid groups.

EXAMPLE 2 (Comparative)

Ethyleneamine E-100* (12.5 g) and 12.5 g of deionized water were added to a 500-ml round-bottom reaction flask equipped as described in Example 1. Approximately 110 g of concentrated hydrochloric acid solution and 31.1 g (0.38 mole) of phosphorous acid were added to the reaction flask and heated to reflux and maintained for one hour.

*Ethyleneamine E-100 is a product of The Dow Chemical Company and is described as a mixture of pentaethylenehexamine plus heavier ethyleneamines with an average molecular weight of 250–300.

Aqueous 37% formaldehyde solution (26.8 g, 0.33 mole) was weighed into the addition funnel and added over a one-hour period. The reaction mixture was heated at reflux for an additional three hours and then cooled. The product was the derivative of E-100 in which all amine hydrogens had been replaced with methylenephosphonic acid groups.

EXAMPLE 3

Ethyleneamine E-100* (12.5 g) and 12.5 g of deionized water were added to a 500-ml round-bottom reaction flask as in Example 2 and heated to 90° C. A 50% aqueous solution of 3-chloro-2-hydroxypropyltrimethylammonium chloride (12.0, 0.032 mole) was weighed into the addition funnel and added over about a 10-minute period. The reaction mixture was heated for an additional hour at 90° C. and cooled. Approximately 110 g of concentrated hydrochloric acid solution and 28.5 g (0.35 mole) of phosphorous acid were added to the reaction flask and heated to reflux and maintained for one hour. Aqueous 37% formaldehyde solution (24.5, 0.30 mole) was weighed into the addition funnel and added over a one-hour period. The reaction mixture was heated at reflux for an additional three hours and then cooled. The product was the E-100 derivative in which ~10% of the amine hydrogens had been replaced with hydroxypropyltrimethylammonium chloride groups, the remainder being replaced with methylenephosphonic acid groups.

*Ethyleneamine E-100 is a product of The Dow Chemical Company and is described as a mixture of pentaethylenehexamine plus heavier ethyleneamines with an average molecular weight of 250–300.

EXAMPLE 4 (Comparative)

An aqueous polymeric polyalkylenepolyamine (PAPA) solution (66.4 g of 36%), prepared from ethyleneamine E-100 and ethylene dichloride, was added to a 500-ml round-bottom reaction flask equipped as in Example 1. Approximately 40 g of concentrated hydrochloric acid solution and 49.3 g (0.60 mole) of phosphorous acid were added to the reaction flask and heated to reflux and maintained for one hour. Aqueous 37% formaldehyde solution (51.1 g, 0.63 mole) was weighed into the addition funnel and added over a one-hour period. The reaction mixture was heated at reflux for an additional one and one-half hours and cooled. The product was the PAPA in which all amine hydrogens had been substituted with methylenephosphonic acid groups.

EXAMPLE 5

The polymeric polyalkylenepolyamine used in Example 4 was modified by reacting ten mole percent of the available aminohydrogens with 3-chloro-2-hydroxypropyltrimethylammonium chloride in a similar manner as described in Example 3. The resultant reaction product was then phosphonomethylated with phosphorous acid and formaldehyde in the presence of hydrochloric acid. The product was the PAPA in which ~10% of the amine hydrogens had been replaced with hydroxypropyltrimethylammonium chloride groups, the remainder being replaced with methylenephosphonic acid groups.

The products of Examples 1–5 were evaluated according to the following scale inhibition test with respect to calcium carbonate: Several 50-ml samples of a 0.02M $CaCl_2$ solution are placed in 4-ounce bottles. To these solutions is added the candidate inhibitor in various concentrations. Fifty-ml samples of a 0.04M sodium bicarbonate/0.96M sodium chloride solution are then added with stirring. A total hardness determination is made on the mixture by adding excess standard EDTA to a sample and back titrating with standard $Mg^{++}$ solution in the presence of Eriochrome Black T indicator. The samples are placed in an 80° C. oven and 10-ml samples taken periodically from each bottle, filtered through a millipore filter, and the total hardness of the filtrates determined by titration. A blank with no inhibitor is run in an identical manner. The relative inhibition effects are shown by determining the amount of hardness (as soluble calcium) before and after heating for a 24-hour period. The amount of soluble calcium as a percent of that originally present is indicated as % inhibition.

Results of these tests are shown in Table I and compared with the phosphonated, but unquaternized amine. All products and comparative runs were made using a concentration of 10 ppm based on active acid.

TABLE I

| Additive | % Inhibition |
| --- | --- |
| $EDA(CH_2PO_3H_2)_4$ (comp.)* | 41.8 |
| Product Ex. 1 | 41.8 |
| Product Ex. 2 (comp.) | 43.4 |
| Product Ex. 3 | 49.9 |
| Product Ex. 4 (comp.) | 35.0 |
| Product Ex. 5 | 38.1 |
| Blank (no additive) | 12** |

*This phosphonate is a commercially available compound sold for the purpose of scale inhibition.
**This indicates that 88% of the calcium had precipitated in the blank.

In the above tests it can readily be seen that the methylenephosphonic acid derivatives which contain at least one quaternary group are at least as good or better than the compounds containing only the methylenephosphonic group, including the derivative of EDA indicated as a commercially available scale inhibition compound. It should be understood that such compounds which contain only the quaternary groups do not exhibit any threshold effect, but that the methylenephosphonic acid group or its salt must be present for the effect to be obtained.

Reactants used to prepare the products of the invention are ammonia, alkyleneamines, polymeric amines and polyethyleneimines of different molecular weights, such as those from Cordova Chemical Company. Various metal and alkali metal salts, ammonium and amine salts and partial salts of the methylenephosphonic acids and mixtures thereof can be utilized to make the quaternized derivatives of the invention. It should be noted, however, that the quaternization of the amine preferably shoud precede the phosphonomethylation and the making of any of the methylenephosphonic acid salts.

Almost any amine that contains reactive aminohydrogens can be utilized to prepare the products. Thus for example, polyglycolamines, amidoamines, oxyalkylated amines, carboxymethylated amins, methylenesulfonated and hydroxypropylsulfonated amines, nitrogenheterocyclics, and the like can be employed as a reactant. The preferred products are those that have had the aminohydrogens fully replaced although some aminohydrogens can be left unreacted.

While the examples all show the use of the chloride form of the quaternary group, other halides, e.g. Br$^-$ or I$^-$, can be employed as the quaternized derivative. Thus, the quaternary salt could be hydroxypropyltriethylammonium bromide, hydroxypropyltripropyl ammoniumiodide and the like.

We claim:

1. A process for inhibiting scale formation in an aqueous solution containing alkaline earth metal ions which comprises adding to said aqueous solution a threshold amount of a compound having the formula

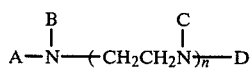

wherein the A, B, C and D substituents are independently selected from the group consisting of hydrogen, methylenephosphonic acid or salt thereof and 2-hydroxy-3 (trialkylammonium halide) propyl wherein each alkyl has from 1 to 5 carbon atoms, n is 0 to 15, and wherein said substituents include at least one methylenephosphonic acid group, or salt thereof, and at least one 2-hydroxy-3 (trialkylammonium halide) propyl group.

2. The process of claim 1 wherein the compound employed has the formula wherein n is 1 and one of A, B, C or D is a 2-hydroxy-3 (trialkylammonium halide) propyl group and the remaining substituents are methylenephosphonic acid groups.

3. The process of claim 2 wherein the methylenephosphonic acid groups are present in the form of a salt of the acid.

4. The process of claim 3 wherein the salt is a sodium salt.

5. The process of claim 1 wherein the compound employed has the formula wherein n is 0 and one of A, B, or D is a 2-hydroxy-3 (trialkylammonium halide) propyl and the remaining two substituents are methylenephosphonic acid groups or salts thereof.

6. The process of claim 5 wherein the methylenephosphonic acid groups are present in the form of a salt of the acid.

7. The process of claim 6 wherein the salt is a sodium salt.

* * * * *